US012629307B2

(12) United States Patent
Joshi et al.

(10) Patent No.: US 12,629,307 B2
(45) Date of Patent: May 19, 2026

(54) APPARATUS AND METHOD FOR POSITIONING A PATIENT'S BODY AND TRACKING THE PATIENT'S POSITION DURING SURGERY

(71) Applicant: Erbe Vision GmbH, Wurmlingen (DE)

(72) Inventors: Shirish Joshi, Wurmlingen (DE);
Faisal Kalim, Reutlingen (DE);
Subhamoy Mandal, Kolkata (IN)

(73) Assignee: ERBE VISION GMBH, Wurmlingen (DE)

( * ) Notice: Subject to any disclaimer, the term of this patent is extended or adjusted under 35 U.S.C. 154(b) by 424 days.

(21) Appl. No.: 17/972,153

(22) Filed: Oct. 24, 2022

(65) Prior Publication Data

US 2023/0130653 A1 Apr. 27, 2023

(30) Foreign Application Priority Data

Oct. 25, 2021 (EP) .................................... 21204576

(51) Int. Cl.
*A61G 13/12* (2006.01)
*A61B 5/107* (2006.01)
(Continued)

(52) U.S. Cl.
CPC .......... *A61G 13/128* (2013.01); *B29C 64/386* (2017.08); *B33Y 50/00* (2014.12);
(Continued)

(58) Field of Classification Search
CPC ...... A61G 13/128; B33Y 50/00; B33Y 80/00; B29C 64/386; A61B 2034/2072;
(Continued)

(56) References Cited

U.S. PATENT DOCUMENTS 7,024,237 B1 * 4/2006 Bova .................... A61N 5/1049
606/130
9,433,387 B2 9/2016 Ahn
(Continued)

FOREIGN PATENT DOCUMENTS

BR 112020022649-1 A2 2/2021
CA 2990825 A1 12/2015
(Continued)

OTHER PUBLICATIONS

Max J. Zinser, Hermann F. Sailer, Lutz Ritter, Bert Braumann, Marc Maegele, Joachim E. Zöller, A Paradigm Shift in Orthognathic Surgery? Journal of Oral and Maxillofacial Surgery, vol. 71, Issue 12, (Year: 2013).*
(Continued)

*Primary Examiner* — Huy Q Phan
*Assistant Examiner* — Martin Walter Braunlich
(74) *Attorney, Agent, or Firm* — Fitch, Even, Tabin & Flannery LLP

(57) ABSTRACT

The disclosed system uses a body shape capturing device for acquiring a patient's body shape and a 3D shape generating device for additively manufacturing a patient receiving device that is at least partially adapted to the patient's body shape or at least partially deviates from the patient's body shape bringing the patient's body into a desired shape so that the outer shape of the patient's body during surgery is identical to the outer shape of the body during shape capturing. The patient receiving device comprises at least one tracker element that is detectable by a detection system. The detection system captures data indicating the at least one tracker element's position and/or orientation during surgery enabling, particularly for surgical operations on or in soft tissues with high flexibly and with no specific natural or
(Continued)

artificial landmarks, the surgeon to orientate/navigate in live images from the surgical site.

13 Claims, 7 Drawing Sheets

(51) Int. Cl.

| | |
|---|---|
| *A61B 34/20* | (2016.01) |
| *B29C 64/386* | (2017.01) |
| *B29L 31/00* | (2006.01) |
| *B33Y 50/00* | (2015.01) |
| *B33Y 80/00* | (2015.01) |

(52) U.S. Cl.
CPC ............. *B33Y 80/00* (2014.12); *A61B 5/1077* (2013.01); *A61B 2034/2072* (2016.02); *B29L 2031/7546* (2013.01)

(58) Field of Classification Search
CPC .................. A61B 5/1077; A61B 34/20; A61B 2034/2055; A61B 2034/2063; A61B 2090/373; A61B 2090/3762; A61B 2090/378; A61B 17/15; A61B 2090/3937; B29L 2031/7546; G06T 2207/30204; A61N 5/1049; A61N 5/1037
See application file for complete search history.

(56) References Cited

U.S. PATENT DOCUMENTS

| | | | | |
|---|---|---|---|---|
| 11,129,681 | B2 * | 9/2021 | Amiot .................... | G16H 40/60 |
| 11,622,818 | B2 * | 4/2023 | Siemionow ............. | G06F 3/012 |
| | | | | 600/408 |
| 11,666,407 | B2 * | 6/2023 | Hladio ................... | A61B 90/14 |
| | | | | 606/130 |
| 11,707,330 | B2 * | 7/2023 | Weinstein .............. | A61B 34/20 |
| | | | | 606/86 R |
| 11,779,423 | B2 * | 10/2023 | Roh ........................ | A61B 90/37 |
| | | | | 606/1 |
| 12,279,826 | B2 * | 4/2025 | Barabás ........... | A61B 17/32053 |
| 2002/0049375 | A1 | 4/2002 | Strommer et al. | |
| 2014/0330417 | A1 | 11/2014 | Keane | |
| 2015/0047652 | A1 | 2/2015 | De Mooij | |
| 2016/0249987 | A1 | 9/2016 | Hladio et al. | |
| 2017/0112577 | A1 | 4/2017 | Bonutti et al. | |
| 2018/0310894 | A1 | 11/2018 | Gallant et al. | |
| 2019/0105423 | A1 | 4/2019 | Moy et al. | |
| 2020/0214598 | A1 | 7/2020 | Li et al. | |
| 2021/0090716 | A1 | 3/2021 | Deasy et al. | |
| 2021/0192759 | A1 | 6/2021 | Lang | |
| 2022/0280247 | A1 * | 9/2022 | Franitza ................. | A61B 34/20 |
| 2023/0058297 | A1 * | 2/2023 | Sethuraman ........... | G06F 30/10 |
| 2023/0338746 | A1 * | 10/2023 | Kimura .................... | A61N 5/10 |
| 2023/0372050 | A1 * | 11/2023 | Blondel ................. | A61B 90/36 |

FOREIGN PATENT DOCUMENTS

| | | | | |
|---|---|---|---|---|
| CN | 103037789 A | 4/2013 | | |
| CN | 107137827 A | 9/2017 | | |
| CN | 107438512 A | 12/2017 | | |
| CN | 108421173 A | 8/2018 | | |
| CN | 109152618 A | 1/2019 | | |
| CN | 112105303 A | 12/2020 | | |
| CN | 113440738 A | 9/2021 | | |
| EP | 3278759 A1 * | 2/2018 | ............. | A61B 34/10 |
| JP | 2007-507246 A | 3/2007 | | |
| JP | 2017-169678 A | 9/2017 | | |
| JP | 2018-532498 A | 11/2018 | | |
| JP | 2019-510599 A | 4/2019 | | |
| RU | 2 720 841 C1 | 5/2020 | | |
| WO | 2020249513 A1 | 12/2020 | | |
| WO | 2021/177421 A1 | 9/2021 | | |

OTHER PUBLICATIONS

V. Edward, et al., "Quantification of fMRI Artifact Reduction by a Novel Plaster Cast Head Holder", Human Brain Mapping, 11:207-213 (published online Sep. 2000, Wiley-Liss, Inc.), 7 pages.

International Extended Search Report for EP Application No. 21204576. 9; dated Apr. 8, 2022; 8 pages.

Federal Institute of Industrial Property; Russian Office Action in corresponding Russian Patent Application No. 2022 127 431, dated Aug. 26, 2025; 10 pages.

Federal Institute of Industrial Property, Russian Search Report in corresponding Russian Patent Application No. 2022 127 431, dated Aug. 26, 2025; 4 pages.

Federal Public Service Ministry Of Development, Industry, Commerce And Services National Institute Of Industrial Property; Brazilian Office Action and Search Report in corresponding Brazilian Patent Application No. BR102022020665-1; dated Sep. 1, 2025; 12 pages.

Japan Patent Office; Notice of Reasons for Refusal in corresponding Japanese Patent Application No. 2022-168250, dated Oct. 8, 2025; 17 pages.

China National Intellectual Property Administration; Notice of First Review Opinion in corresponding Chinese Patent Application No. 202211309104.1, dated Nov. 28, 2025; 26 pages.

* cited by examiner

APPARATUS AND METHOD FOR POSITIONING A PATIENT'S BODY AND TRACKING THE PATIENT'S POSITION DURING SURGERY

CROSS REFERENCE TO RELATED APPLICATION

This application claims the benefit of European Patent Application No. 21204576.9, filed Oct. 25, 2021, which is incorporated herein by reference in its entirety.

TECHNICAL FIELD

The invention relates to an arrangement for positioning a patient's body and tracking the patient's position during surgery.

BACKGROUND

U.S. Pat. No. 9,433,387 B2 discloses a system for obtaining cranial or other scans from a patient. The system comprises a diagnostic scanning table and a mold that conforms to a portion of a patient's body contour. In one embodiment a mask for encompassing the patient's head is provided. Sensors are placed within the mold or mask for obtaining pressure readings, which may indicate movements of the patient such as a swallowing action. The signals of the sensors may be used for avoiding inaccuracies during the scan due to movements of the patient. For doing so, the sensors are coupled to the scanning system.

Furthermore, US 2019/0105423 A1 discloses the support for a patient's limb. This support comprises a network of flexible multi lumen tubing interlaces, which form a lattice structure. By inflating the multi lumen tubing a limp says within the support may be immobilized.

The article V. Edward, C. Windishburger et al., Quantification of fMRI Artifact Reduction by a Novel Plaster Cast Head Holder (published online September 2000), Wiley-Liz, Inc. discloses a plaster cast head holder for immobilization and repositioning a patient's head during an fMRI scan. The plastic cast head holder will decrease the magnitude of unintentional head movements and reduce movement artifacts. The plastic cast head holder comprises a head mask with malleable fixation material, which is stiff in its fully hardened state.

While there is a wide variety of techniques for acquiring images from patient's body before surgery, as for example ultrasonic imaging radioscopy, computer tomography (CT), or magnetic resonance imaging (MRI), the surgeon may still have problems with identifying objects and tissues viewed with the camera during surgery.

In US 2016/0249987 A1 a sensor is attached to an anatomy of the patient before the surgery whereas during surgery a computing unit is in communication with the sensor enabling to register the patient's anatomy during surgery. The patient's anatomies used for attaching the sensor are for instance bones or relatively rigid organs. This approach, however, requires additional invasive surgical interventions before the actual surgery, which means additional costs as well as additional physical strain for the patient. Also the patient's soft tissues such as muscles, tendons, ligaments, fat, fibrous tissue, lymph and blood vessels can deform during a repositioning of the patient's body, viz. a change of the position and/or orientation of the patient's body or parts of the patient's body. A repositioning can result in a redistribution of weights, which in turn can result in deformation of the patient's body. Therefore, there is a strong desire to obviate the above-mentioned problems and help the surgeon to orientate during surgery.

SUMMARY

This objective is solved by the arrangements and by the methods disclosed herein.

The inventive arrangement comprises a body shape capturing device, a processing unit, a 3D shape generating device and a localization or detection system. The body shape capturing device is adapted to acquire a (outer contour) shape of at least a part of the patient's body. The processing unit is adapted to generate a data representation of the patient receiving device adapted to at least partially receiving a patient's body. The data representation of the receiving device is generated based on the patient's shape. The term patient's shape may be understood as the outer contour of his or her body. The 3D shape generating device is adapted to additively manufacture at least parts of the patient receiving device based on the data representation. For example, the shape generating device can be a 3D printing device. The patient receiving device comprises at least one tracker element that is connected to the (patient receiving) device and adapted to indicate the position and orientation of the patient receiving device. The localization or detection system is adapted to capture data indicating the at least one tracker element's position and/or orientation during surgery. The patient's body shape scan can be performed before any medical scan or live scan is performed gathering the (outer contour) shape of at least a part of the patient's body.

Alternatively, the shape of the patient's body part can be directly obtained from a medical scan without the necessity of performing a shape scan beforehand, e.g. utilizing an automatic skin segmentation of the body part in the medical scan. Obtaining the shape of the patient's body part directly from a medical scan can reduce the risk of further changes of the position of the patient's body part from the medical scan to the surgery. A mechanical scanner, a laser scanner, structured light illumination and camera system, a stereoscopic or multi camera system or any other suitable shape acquiring device can be used for scanning the shape of the body or at least a part thereof. The so acquired data characterizing the patient's body shape are used in a processing unit to generate a data representation of the patient receiving device. An inner shape of the patient receiving device can be adapted to the (outer counter) shape of the patient's body. Alternatively or additionally, at least parts of the inner shape of the patient receiving device can deviate from the precise outer contour shape of the patient's body enabling to reposition at least parts of the patient's body and/or or redistribute the weight of the patient's body e.g. by reforming parts of the patient's soft tissue.

The 3D shape generating device can in particular print a plaster, a fiber glass or a resin based cast creating a three-dimensional structure. This process can enable a better fitting of the patient receiving device to the patient's body by removing constructional limitations in designing the patient receiving device. The inventive concept can further enable including movably connected structures/parts such as cover structures for surgical windows and/or joints enabling easy attachment and removal of the patient receiving device from the patient's body.

The patient receiving device will be used for positioning and/or shaping the patient during the surgical procedure in the same shape or in a corrected shape as it was during a medical imaging.

The at least one tracker element is connected to the patient receiving device and is adapted to indicate the position and orientation of the patient receiving device. In other words, the at least one tracker element is adapted to indicate the location (X, Y, Z) of at least one point in space of the receiving device in combination with free orientations (angular orientation around axes X, Y, Z). Alternatively, two or more tracker elements may be provided for indicating the spatial position and orientation of the patient receiving device.

Furthermore, the arrangement comprises a localization or detection system for capturing data indicating the position and orientation of any of the tracker elements in example cameras, a CT scanner, an x-ray apparatus or any other arrangement or medical imaging device.

In a second embodiment the arrangement further comprises:

A medical imaging system, a live imaging device and a computation unit. The medical imaging system is adapted to acquire at least one at least two dimensional medical image of the patient's region of interest in relation to the at least one tracker element. The images may be acquired in a preoperative scan or even during surgery. The tracker's attachment to the patient receiving device may be localized or detected therewith. A medical imaging device may comprise a processing unit, which generates the scan image within a coordinate system with that tracker elements located in the same coordinate system.

At the operation site the localization or detection system is provided for capturing data indicating the tracker's position and/or orientation during surgery. The data regarding the position and/or orientation of the trackers may be captured by at least one tracking camera. The camera might or might not be close to the surgical site but kept at a distance. However, line of sight visibility should be ensured.

Alternatively, an active tracking method may be used where the patient receiving device may emit at least one signal such as a radio frequency (RF) signal, a light signal or an ultrasonic signal. The signal of the patient receiving device can be received and used for capturing/obtaining the patient receiving device position and/or orientation during surgery. For example RF trackers can be embedded in the patient receiving device during or after manufacturing. In that case the data are captured/transmitted from the site the trackers are placed.

Since the patient is placed within the same individually shaped portion of the patient receiving device as he or she was during the medical imaging process, the patient's body will take the same shape surgery as it had during the medical scan. Therefore, the data captured by the localization or detection system precisely indicates the position and orientation of the patient receiving device and hence the position of tissue structures of the patient. The shape adaptive receiving device will now reshape the patient's body and make sure that all tissues of the patient are in the same place as they have been during the medical scan. This is in particular important for surgical operations on or in soft tissues with high flexibly and with no specific natural or artificial landmarks. The computation unit may register and blend the scan image and the live image and provide perfect orientation for the surgeon. In particular, the inventive system provided the following advantages:

1. There is no need for preoperative interventions for implanting tracking markers or markings inside the patient's body.
2. There is no need for using screws, pins or the like in bones or target structures. Therefore, additional surgical procedure and potential complications can be avoided.
3. There is reduced or even no need for using additional medical imaging devices during the surgical operation.
4. The inventive method and system do not rely on rigid anatomies (as there are bones) or organs with though deformation.

The invention avoids changes in the contour of a patient's torso due to redistribution of the weight caused by changing the patient's outer contour or position. Therefore, the invention allows for acquiring medical images and performing the surgical procedure afterwards. The surgical procedure may be performed in a position of the patient different from the position during medical imaging.

In particular, the processing unit is further adapted to compute the at least one outer contour shape using the medical scan image so that a separate shape scanning of the patient's body can be avoided.

Preferably, the patient receiving device comprises a movable table and an additively manufactured structure that is placeable on, and connectible to, the movable table. The additively manufactured structure may be removably connected to the movable table. The movable table can support the patient's body.

In particular, the 3D shape generating device is adapted to additively build the additively manufactured structure which can be placed on and removably connected to an upper surface of the movable table. Alternatively, the additively manufactured structure is built separately in several pieces and assembled together after building.

Preferably, an inner shape of the additively manufactured structure is at least partly adjusted to the patient's outer contour shape. This allows the patient's position and/or orientation from the medical scan to be maintained and/or re-established for surgery.

Additionally or alternatively, an inner shape of the additively manufactured structure may at least partially deviate from the outer contour shape bringing the patient's body into a desired position, orientation, and/or shape. This allows for bringing the patient's body or at least parts of the patient's body into a position, orientation and/or shape that in turn allows the surgeon to have better access to regions of interest during surgery compared to the original position, orientation and/or shape.

Moreover, the additively manufactured structures may comprise at least two pieces that are configured to be assembled, disassembled, and/or reassembled. So a faster building process and lower complexity of the individual parts results. A receiving structure may also be easier removed or reassembled.

Preferably, the receiving device may comprise an opening that exposes the surgical sites. The opening allows for easy access to the surgical site. The opening may comprise a cover flap that enables to open or close the opening.

Preferably the tracker element is adapted to indicate the position and orientation of the patient receiving device in space. The at least on tacker element is firmly connected to the receiving device. The detection system may be placed at the surgical site of the arrangement and comprises preferably at least two cameras or other positional detectors for trigonometrically determining the place (and if necessary the orientation) of the at least one tracker element in space. The detection system can be adapted for performing a triangulation measurement determining the tracker element's position in space. Moreover, an imaging system may comprise at least one tracker element or any other sensor connected to a detection system adapted to detect localization and orientation of the camera. The detection system may be connected to the computation unit, which accordingly may register the live image and the scan image.

Furthermore, the computation unit may comprise a structure detecting unit for generating graphical representations of tissue structures. The graphic representations may be obtained from the medical images. The graphical representations may be lines, symbols, colored areas or anything else adapted to indicate regions or tissues the surgeon shall distinguish from other regions or tissues. These graphical structures may be blended into the live images, which helps the surgeon to find structures to be treated within the region of interest.

Preferably, the 3D shape generating device is adapted to additively build the at least one tracker element, wherein the at least one tracker element is connectable to a (upper surface) of the movable table and/or a (upper) surface of the additively manufactured structure. Alternatively, if the tracker element is an active tracker, the at least one tracker element may be embedded in the patient receiving structure. If the tracker element is a passive tracker, the tracker element may comprise reflector elements that are spaced apart one from another and detectable by the detection system.

Preferably, the detection system comprises at least two cameras for trigonometrically determining the place and the orientation of the at least one tracker element and space. Alternatively, the detection system may comprise a 3D camera acquiring image as well as depth information.

In a specific embodiment, the arrangement may involve an instrument for treating the patient's body in the region of interest. The instrument may be any type of RF surgical, cryosurgical, plasma surgical or any other surgical instrument. In particular, the instrument is adapted to be placed within the field of view of the live imaging device. The live imaging device may be part of the instrument, a separate camera inserted into a trocar, or a separate camera placed at, on, or in the patient's body.

The inventive method comprises the steps of:

Acquiring an outer contour shape of at least a part of the patient's body;

Generating, based on the outer contour shape, a data representation of a patient receiving device at least partially receiving the patient's body;

Additively manufacturing at least parts of the patient receiving device based on the data representation;

Connecting at least one tracker element of the patient receiving device that indicates the position and orientation of the patient receiving device; and Capturing data indicating the at least one tracker elements positon during surgery.

Preferably, the manufacturing of the patient receiving device comprises additively building an additively manufactured structure comprising an inner shape that is at least partly adjusted to the (outer contour) shape of the patient's body and/or partly deviates from the (outer contour) shape bringing the patient's body into a desired position, orientation and/or shape.

The features and advantages that are mentioned with respect to the arrangement also apply to the inventive method.

Further details and features may be found in the drawings, the description and the claims as well.

DETAILED DESCRIPTION

Figure 1:
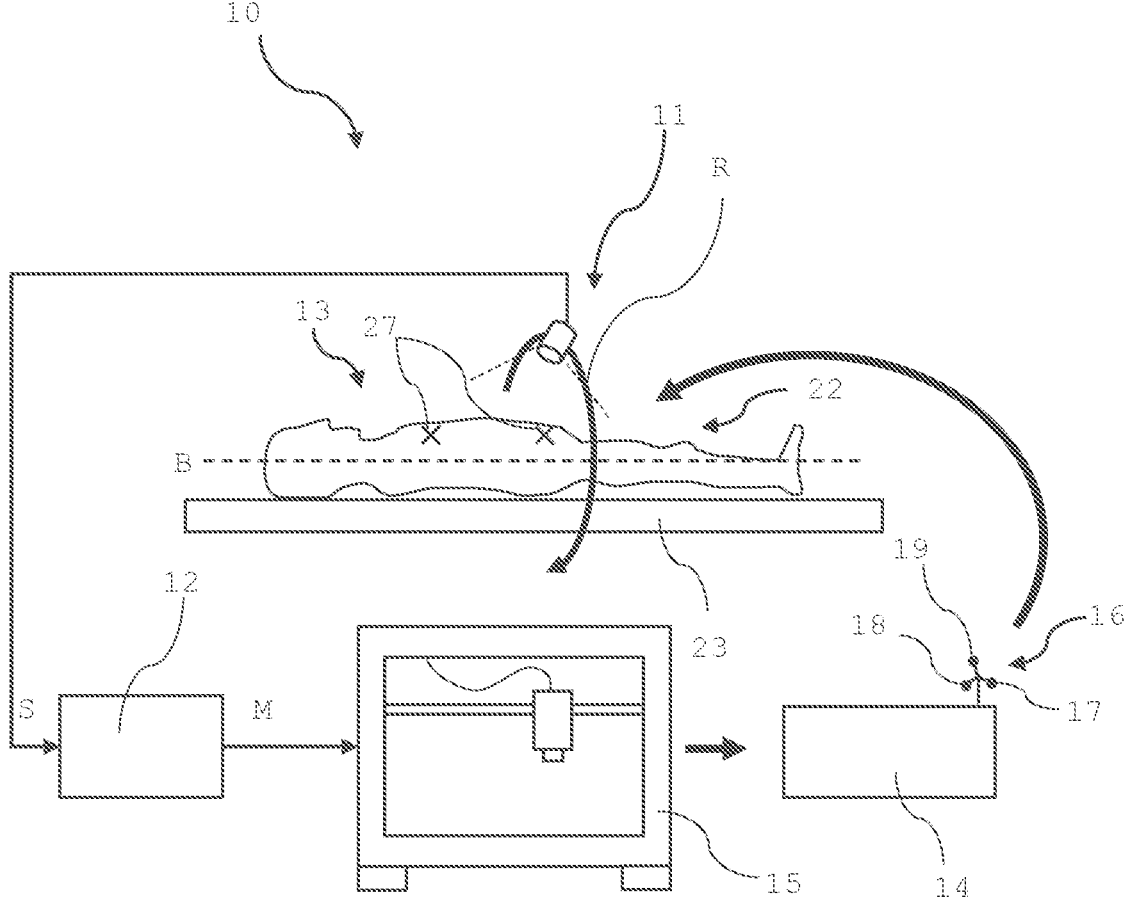
FIG. 1 is a schematic representation of a patient receiving device with a patient placed therein in the body shape capturing device.

FIG. 1 illustrates an arrangement for body shape capturing 10 comprising a body shape capturing device 11 adapted to acquire a shape S of at least a part of the patient's body 13. The patient 22 is placed on a movable table 23. In FIG. 1, the body shape capturing device 11 is a 3D camera that acquires image and simultaneously depth information. The body shape capturing device 11 is rotated around a patient's body length axis B which is indicated by the arrow R. The body shape capturing device 11 is communicatively connected to a processing unit 12 adapted to generate a data representation (model) M of a patient receiving device 14 based on the patient's body shape S. The patient receiving device 14 is adapted to at least partially receive the patient's body 13. A 3D shape generating device 15 is communicatively connected to the processing unit 12. In the present example, the 3D shape generating device 15 is a 3D printing device 15 that receives the model M of the patient receiving device 14 from the processing unit 12. The 3D printing device 15 is adapted to additively manufacture the patient receiving device 14 based on the received model M.

The patient receiving device 14 comprises at least one tracker element 16 that is firmly connected to the patient receiving device 14. The tracker element 16 is adapted to indicate the position and orientation of the patient receiving device 14. In the present example there are three tracker element portions 17, 18, 19 which in the present case are balls fixed at the ends of a tree 20 in known distances one from another. Balls 17a, 18a, 19a may be light reflecting or light absorbing balls visible ball the imaging system 21. In the present case three tracking element portions 17, 18, 19 are provided for unambiguously indicating the location and orientation of the patient. However, while three balls 17a, 18a, 19a placed on the ends of the tree 20 give a fairly good indication of the location and orientation of the patient it is also possible to place three different balls independent from one another at different places of the patient receiving device 14.

If the tracker element portions 17, 18, 19 will be optically detected they will be placed at a visible side of the patient receiving device 14. Furthermore, it is possible to use only one item as a tracker element 16 e.g. one cube firmly connected to the receiving device 14. Other tracker elements having different designs are also well applicable.

After manufacturing, the patient receiving device 14 can be put on or around the desired region of the patient's body so that the patient's body is brought into a desired position, orientation and/or shape. For instance, the desired region of the patient's body 13 may be marked before the shape scan with reference markers 27 that are affixed and/or painted on the patient's body 13. The desired region of the patient's body is the torso of the patient in FIG. 1.

Figure 2:
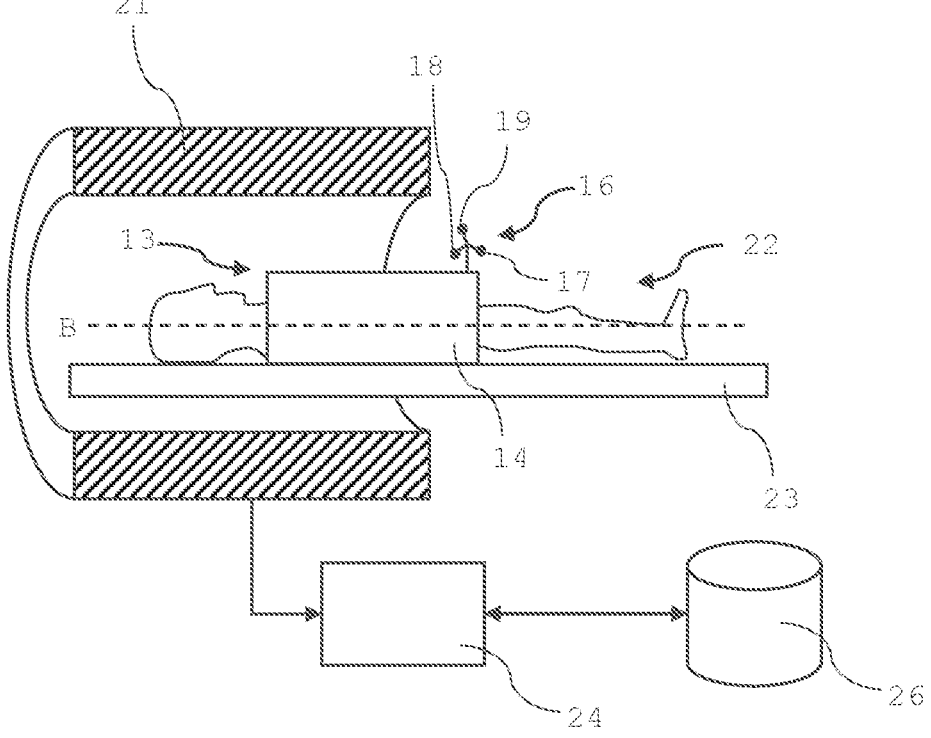
FIG. 2 is the schematic representation of a patient receiving device with the patient placed therein, a medical imaging device and a 3D shape generating device.
Figure 5:
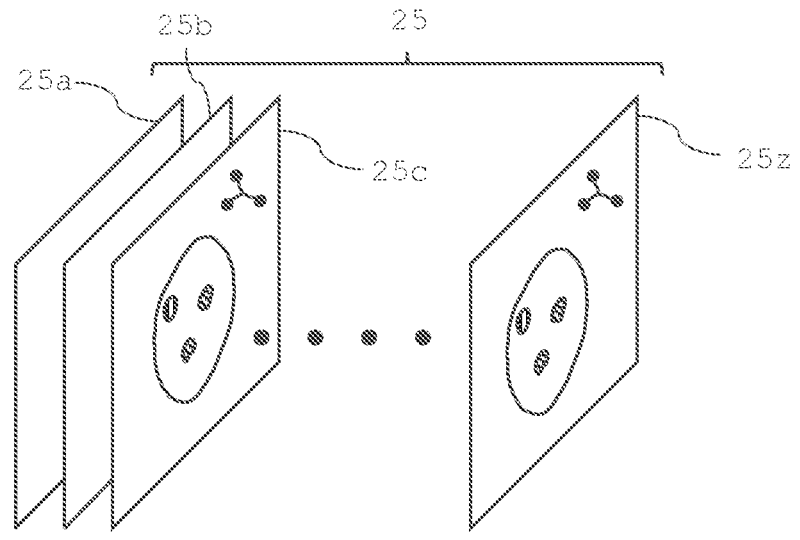
FIG. 5 is a schematic representation of scan images provided by the medical imaging device.

In FIG. 2 of the patient receiving device 14 with a torso of patient 22 placed therein and a medical imaging device 21. The medical imaging device 21 can be any type of medical imaging system for acquiring a pre-operative medical scan as there is a MRI system or a CT system. A CT system may comprise an x-ray source and an x-ray detector adapted to receive x-ray from source and deliver data to a computation unit (an image processing unit) 24 producing scan images 25 (25a to 25z) as illustrated in FIG. 5. The image processing unit 24 may be any type of computer adapted processing signals supplied by the x-ray detector. The image processing unit 24 is connected to storage 26 for storing the scan images 25 therein. Alternatively or additionally, an intraoperative scan apparatus 24a may be provided in example a CR system, an ultrasonic imaging apparatus 24b or any other system suited for providing medical scan images 25 during operation.

A medical imaging system 24 may additionally be used as a means for capturing data indicating the portions of the tracker element 17, 18, 19 during operation of the imaging system in example during the scanning of the patient's body 13. Alternatively, a separate detection system may be provided for detecting and locating the tracking element portions 17, 18, 19 and bringing the images 25 into special relation to the tracking element portions 17, 18, 19.

Figure 3:
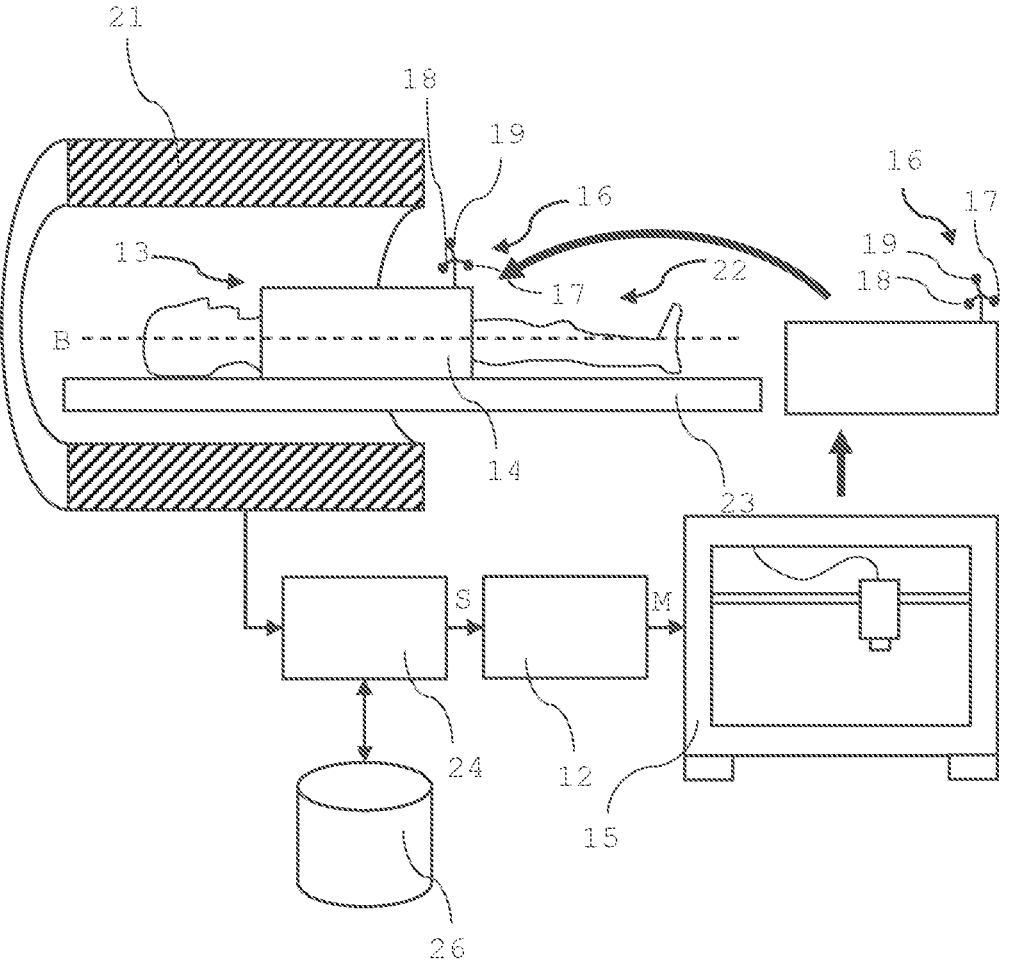
FIG. 3 is the schematic representation of a patient receiving device with the patient placed therein, a medical imaging device and a 3D shape generating device.

FIG. 3 shows the example of FIG. 2, except that no shape scan (as illustrated in FIG. 1) has been performed before the medical scan. The shape S of the patient's body extracted from the scan images 25 in the image processing unit 24. The shape S is provided to the processing unit 12 which generates a (three-dimensional) model M of a patient receiving device 14 that is sent to the 3D printing device 15. The 3D printing device 15 additively manufactures at least parts of the patient receiving device 14. Again, after manufacturing, the patient receiving device 14 can be put on or around the desired region of the patient's body so that the patient's body is brought into a desired position, orientation and/or shape as described above in the context of FIG. 1.

Figure 4:
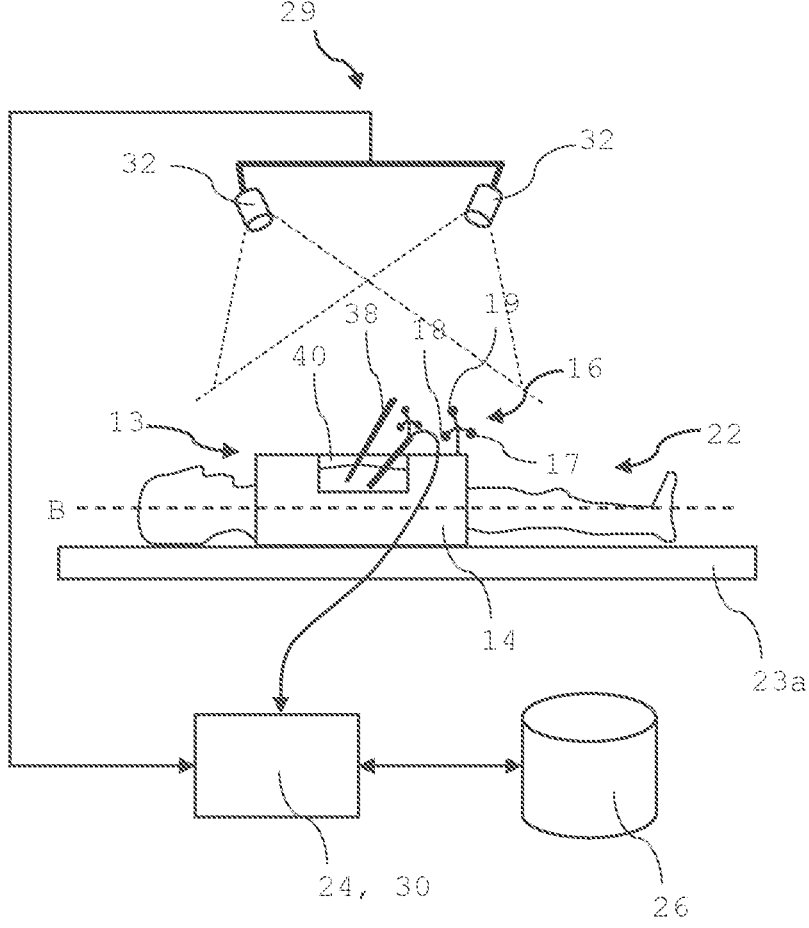
FIG. 4 is a schematic representation of the patient placed in a patient receiving device at the surgical site for the inventive arrangement including a detection system for localizing or detecting the patient during surgery.

Part of the arrangement may be an operation site 28 illustrated in FIG. 4. The patient again is placed on a table, which may be identical with the movable table 23 of the scanning/imaging sites illustrated in FIGS. 1, 2, 3. However, typically table 23a will be a different table as typically used in a regular operating room. No matter whether tables 23, 23a are identical or not, an additively manufactured structure 31 will be used for bringing the patient's body in the same shape as it has had during medical imaging as illustrated in FIGS. 1, 2, 3. Moreover, the tracking element portions 17, 18, 19 will be in the same position relative to the patient's body 13 during imaging/scanning and during surgery as well.

At the operation site 28, a localization or detection system 29 is provided for capturing data fed into a localization or detection processing unit 30 connected to the storage 26. The localization or detection processing unit 30 may be identical with the image processing unit 24 of FIGS. 2, 3 or alternatively it may be a different or separate processing unit. Processing units 24, 30 may be any type of computer or processor adapted to receive data from the detection system 29 and determine the position and orientation of the tracker element portions 17, 18, 19 and hence the positioning and orientation of the patient's body 13. The detection system 29 may comprise at least two cameras 32 oriented such that the tracking element portions 17, 18, 19 are within the combined field of view of the cameras 32. Processing units 30 or 24 are adapted to locate the tracker element portions 17, 18, 19 by triangulation before the surgery starts if the table 23a is kept at rest. If table 23a is moved the detection system 29 may repeat determining the position and orientation of the patient's body 13. Alternatively, the detection may continuously be performed by the detection system 29 during surgery.

Figure 7:
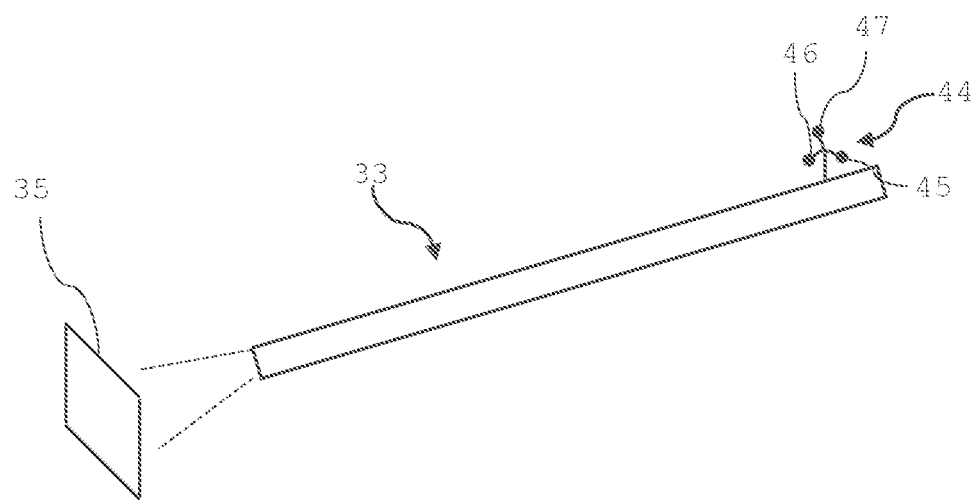
FIG. 7 is a schematic representation of the camera for acquiring live images.
Figure 8:
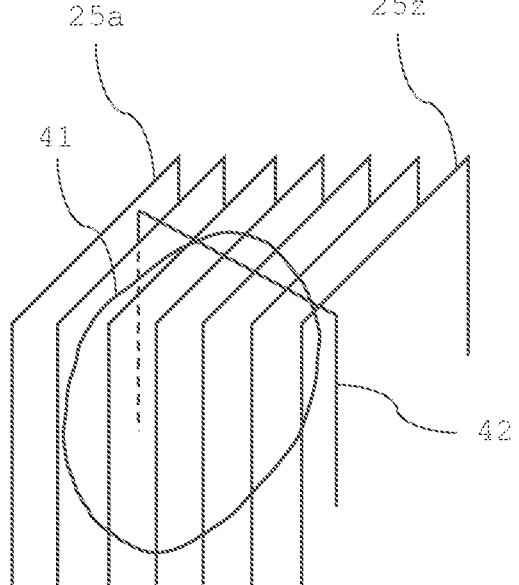
FIG. 8 illustrates the scan images, a volume model of a patient's tissue structure obtained from the scan images, and the live image registered into the spatial representation of the tissue structure.

Part of the arrangement is a live imaging device 33 which can be another camera for acquiring live images as separately illustrated in FIGS. 4 and 7. The field of view 34 of the camera 33 is a region of interest 35 of the patient's body 13 and at which surgery is to be performed. FIG. 8 illustrates the region of interest 35 covered by the field of view 4. The camera 33 may be a laparoscopic camera and endoscopic camera or any other type of cameras suitable and adapted to produce a live image 36 of the region of interest 35.

Figure 6:
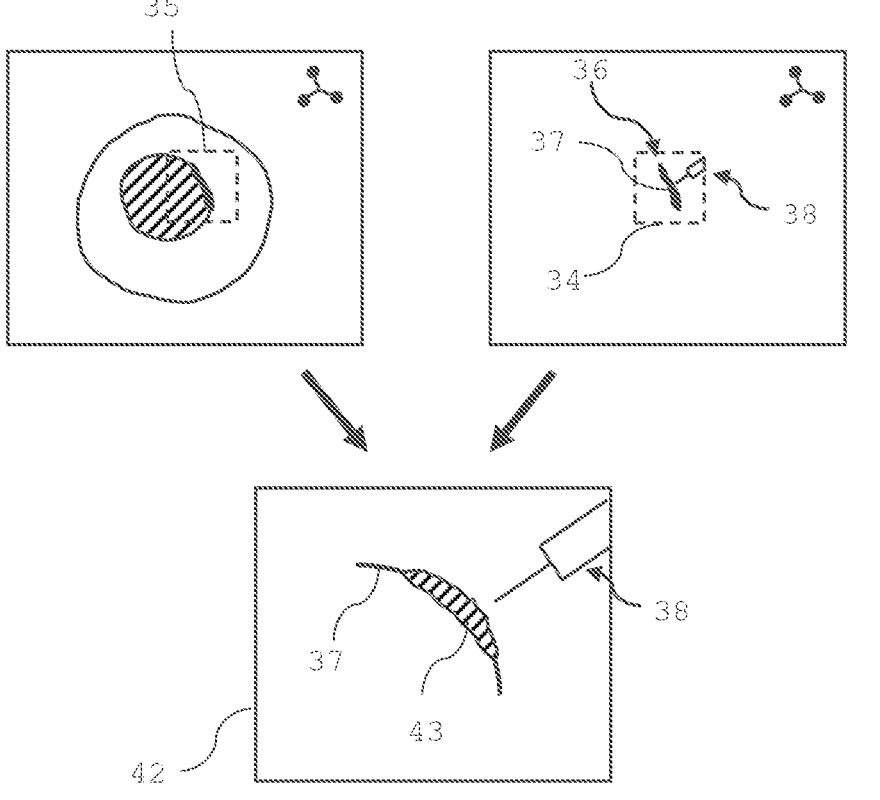
FIG. 6 illustrates the scan image a live image and a blended image provided to the surgeon.

The live image 36 may be fed to the processing units 24, 30 as illustrated in FIG. 4. The processing unit 24, 30 may process any live image 36 which is shown in FIG. 6, right upper illustration. The live image 36 may contain a real tissue structure 37 and the tip of an instrument 38. Any type of detection system may be used for detecting location and/or orientation of the instrument 38 and/or the camera 33. The localization or detection system 39 for localizing the camera 33 may comprise at least one tracker element 44, which may include, for example, three tracker element portions 45, 46, 47 as illustrated in FIG. 7, which are similar to the tracker element portions 17, 18, 19. Other types of tracking systems may be used as well.

Figures 9, 10:
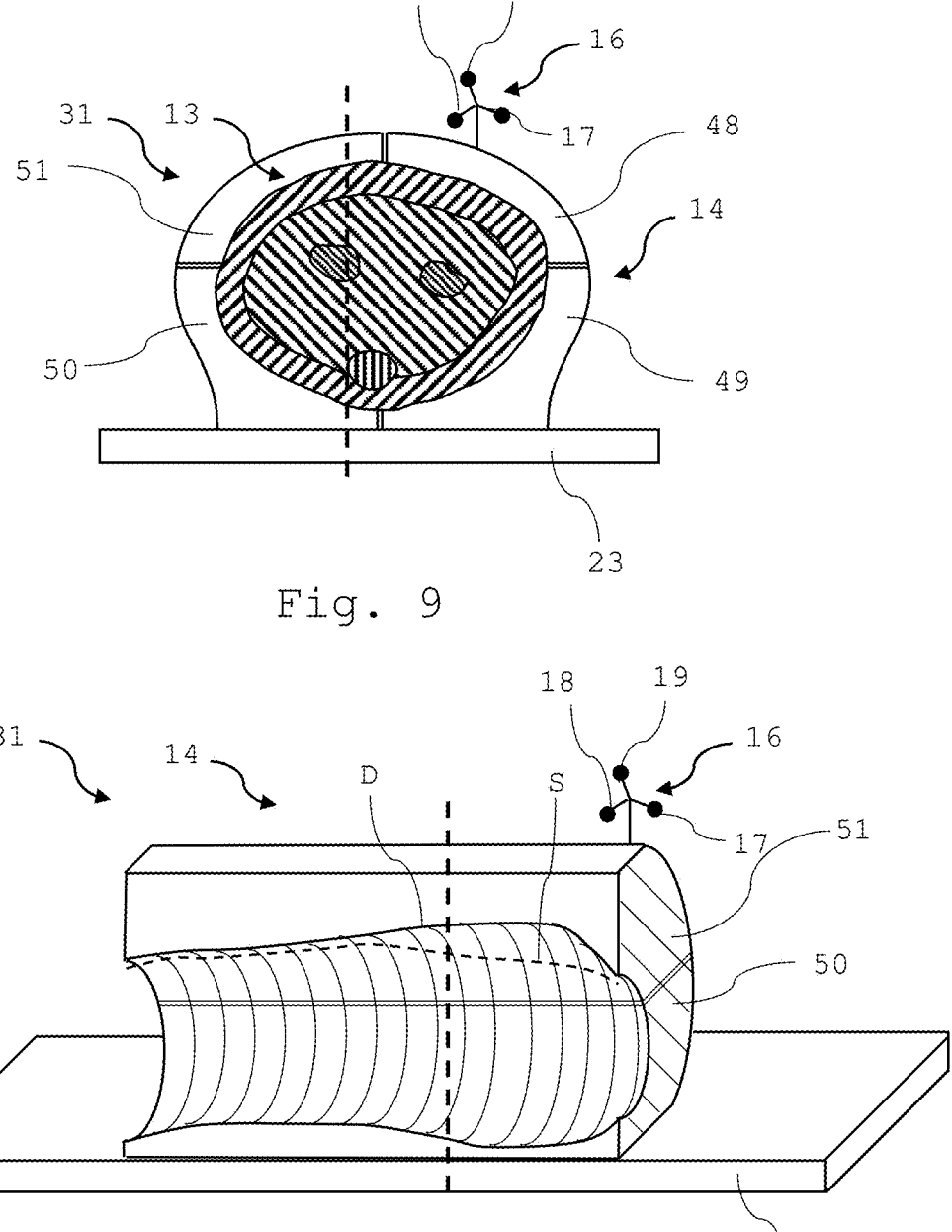
FIG. 9 is a cross-sectional view of patient receiving device and the patient placed therein.
FIG. 10 is a longitudinal-section view of the receiving device.

In FIG. 9 displays a cross-sectional view of patient receiving device 14 and the patient 22 placed therein. The patient receiving device 14 in the example of FIG. 9 comprises an additively manufactured structure 31 that is connected to a movable table 23. The additively manufactured structure 31 for example comprises four parts 48, 49, 50, 51 that can be individually manufactured by additively manufacturing, i.e., 3D printed. The parts 48, 49, 50, 51 can be removably assembled, for instance with locking and/or latching mechanisms at the junctions of the individual parts. The at least one tracker element 16 is firmly connected to an outer surface of the additively manufactured structure 31. As depicted in FIG. 9, the tracker element 16 is connected to one part 48 of the additively manufactured structure 31. The tracker element 16 comprises three balls 17, 18, 19 that are mechanically connected via a tree with the part 48. Alternatively, the additively manufactured structure 31 can be monolithically formed in one part. In this alternative, flaps, joints and/or locking and/or latching mechanisms can be provided to simplify taking on the patient receiving device.

FIG. 10 illustrates a longitudinal-section view of the patient receiving device 14 cut along the dashed line in FIG. 9. FIG. 10 shows the outer contour shape S acquired by a body shape capturing device 11. In order to put the patient 22 into a desired shape D, the inner shape of the additively manufactured structure 31 diverges from the scanned shape S. In the example of FIG. 10, mainly the inner shape of part 51 diverges from the patient's shape S.

The so far described arrangement operates as follows:

Before surgery the patient will be placed on the table 23 and the body shape capturing device 11 acquires a shape S of the patient's body 13 as illustrated in FIG. 1. The processing unit 12 computes a model M for a patient receiving device 14, which is sent to the 3D printing device 15. The 3D printing device 15 prints the patient receiving device 14 based on the received model M. The printed receiving device 14 is then put on the patient and the medical imaging scan such as illustrated in FIG. 2 can be performed. If the processing unit 4 is able to extract the shape S of the patient's body from the medical image the patient receiving device 14 is built by the 3D printing device 15 based on the model M that is extracted from the medical images as illustrated in FIG. 3.

After the patient receiving device 14 is manufactured and put on or around the patient, the imaging system 21 may acquire scan images 25a to 25z, which images are stored by processing unit 24 in the storage 26. Afterwards the patient may leave the receiving device 14 and prepare for surgery, which may follow within a short period of time and sometimes within hours or days.

For surgery the patient reenters the patient receiving device 14 as illustrated in FIG. 4 by placing his or her body at the table 23 with the receiving device placed on or around the body 13 as illustrated in FIG. 4. The patient receiving device 14 may comprise an opening (window) 40 that the surgeon may open before or during surgery. The window 40 may exclusively be designed according to the needs of the surgery or the surgeon. Alternatively, the surgeon may have to cut a window 40 in one or more pieces of the additively manufactured structure elements so that he or she has access to the body through the window 40.

At the beginning or before the beginning of the surgery the detection system 29 will be activated which captures position of the tracking elements 17, 18, 19. So the processing unit 24, 30 will be registered the position of the patient's body to the scan images 25a to 25z as illustrated in FIG. 8. Moreover, the processing unit 24 or the processing unit 30 may produce a volume model 41 of at least a portion of the patient's body in example of the region of interest 35.

The detection system 29 or any other tracking system for determining the position and orientation of the camera 33 continuously processes data from which a processing unit 24, 30 determines the place and orientation of the field 34 of the camera 33 and hence the place of the live image 36 and the viewing direction to the live image. As illustrated in FIG. 8 the live image 36 may intersect the volume model 41 in a different way as the scan images 25a to 25z. However, the processing unit 24, 30 may produce a synthetic image of the volume model 41 as illustrated in FIG. 8, upper left illustration, at least of the region of interest 35. For doing so, the processing unit may intersect the volume model 41 in the same plane as the live image 25.

The processing unit 24, 30 will then merge and blend the live image 42 (FIG. 6, upper right illustration) with the volume model illustration derived by intersecting the volume model 41 at the same place and with the same orientation as has the live image 42. FIG. 6 illustrates the blended image 51 with the tissue structures 43 seen by camera 39 and the specific tissue structure 43 found by the imaging and to be treated by instrument 44.

Furthermore, the processing unit 24 or 30 may alternatively or additionally use graphical presentations 48 of tissue structures and blend those graphic representations 48 into the live image. Any of the scan images 25 the image obtained by intersecting the volume model 41, and a graphic representation 48 obtained from at least one of the scan images or from the volume model 41 are considered being a "scan image" for blending with the "live image". The arrangement further comprises an image display 49 for reproducing the blended image. The display 49 may be a screen, a virtual reality head set or another means for showing the blended image.

The inventive system uses a body shape capturing device for acquiring a patient's body shape and a 3D shape generating device for additively manufacturing a patient receiving device that is at least partially adapted to the patient's body shape or at least partially deviates from the patient's body shape bringing the patient's body into a desired shape so that the outer shape of the patient's body during surgery is identical to the outer shape of the body during shape capturing. The patient receiving device comprises at least one tracker element that is detectable by a detection system. The detection system is adapted to capture data indicating the at least one tracker element's position and/or orientation during surgery enabling in particular important for surgical operations on or in soft tissues with high flexibly and with no specific natural or artificial landmarks the surgeon to orientate/navigate in live images from the surgical site.

REFERENCE NUMERALS 10 arrangement for body shape capturing
11 body shape capturing device
12 processing unit
13 patient's body
14 patient receiving device
15 3D shape generating device (3D printing device)
16 tracker element
17 to 19 individual tracker element portions (balls)
20 tracker tree
21 imaging system
22 patient
23 movable table
23a table for surgery
24 image processing unit
25 scan images
26 storage
27 reference markers
28 operational site
29 localization or detection system
30 localization or detection processing unit
31 additively manufactured structure
32 cameras
33 live imaging device (camera)
34 field of view
35 region of interest
36 live image
37 real tissue structure
38 (surgical) instrument
39 localization or detection system for camera 33
40 opening (window)
41 volume model
42 blended image
43 further tissue structure 44 at least one tracker element of camera 33
45 to 47 individual tracker element portions (balls)
48 graphical representations
49 image display
B length axis of the patient's body
M data representation (model)
R arrow (direction of scanning)
D desired shape
S outer contour shape of the patient's body

What is claimed is:

1. An arrangement for positioning a patient's body and tracking the patient's position during surgery comprising:
   a body shape capturing device (11) adapted to acquire an outer contour shape (S) of at least a part of the patient's body (13);
   a processing unit (12) adapted to generate based on the outer contour shape (S) a data representation (M) for a patient receiving device (14) adapted to at least partially receive the patient's body (13);
   a 3D shape generating device (15) adapted to additively manufacture based on the data representation (M) at least parts of the patient receiving device (14), the patient receiving device (14) comprising at least one tracker element (16) that is connected to the patient receiving device (14) and adapted to indicate a position and orientation of the patient receiving device (14);
   a medical imaging system (21) adapted to acquire at least one at least two-dimensional medical image of a patient's region of interest in relation to the at least one tracker element in a preoperative scan;
   a detection system (29) at an operation site for capturing data indicating the at least one tracker element's position during surgery;
   a live imaging device (33) for acquiring live images of a surgical site; and
   a computation unit (24) configured to generate a volume model of the patient's region of interest from the at least one at least two-dimensional medical image;
   wherein the computation unit is further configured to generate a synthetic cross-sectional image of the volume model in a plane aligned with a plane of a live image and is adapted to register and blend the synthetic cross-sectional image and the live image according to the captured data of the tracker element's position during surgery.

2. The arrangement of claim 1, wherein the processing unit (12) is further adapted to compute the outer contour shape (S) using the at least one medical image (25).

3. The arrangement of claim 1, wherein the patient receiving device (14) includes a movable table (23) and an additively manufactured structure (31) that is configured to be placed on the movable table (23).

4. The arrangement of claim 3, wherein the 3D shape generating device (15) is adapted to additively build the additively manufactured structure (31) as one part.

5. The arrangement of claim 3, wherein an inner shape of the additively manufactured structure (31) is at least partly conformed to the outer contour shape (S) of the patient's body (13).

6. The arrangement of claim 3, wherein an inner shape of the additively manufactured structure (31) at least partly deviates from the outer contour shape (S) for bringing the patient's body into a desired position, orientation and/or shape (D).

7. The arrangement of claim 3, wherein the additively manufactured structure (31) comprises at least two parts (48, 49, 50, 51) that are configured to be assembled, disassembled and/or reassembled.

8. The arrangement of claim 1, wherein the patient receiving device (14) comprises an opening (40) for exposing a region the surgery is to be performed on.

9. The arrangement of claim 3, wherein the 3D shape generating device (14) is adapted to additively build the at least one tracker element (16), wherein the at least one tracker element is configured to be connected to a surface of the movable table (23) and/or a surface of the additively manufactured structure (31).

10. The arrangement of claim 1, wherein the at least one tracker element (16) comprises spaced apart reflector elements detectable by the detection system (29).

11. The arrangement of claim 1, wherein the detection system comprises at least two cameras (37, 38) for trigonometrically determining the position and the orientation of the at least one tracker element (21) in space.

12. A method for positioning a patient's body and tracking the patient's position during surgery comprising:
   acquiring an outer contour shape (S) of at least a part of the patient's body (13);
   generating a data representation (M) of a patient receiving device (14) for at least partially receiving the patient's body (13) based on the outer contour shape (S);
   additively manufacturing at least parts of the patient receiving device (14) based on the data representation (M);
   connecting at least one tracker element (16) to the patient receiving device (14) that indicates the position and orientation of the patient receiving device (14);
   acquiring at least one at least two-dimensional medical image of the patient's region of interest in relation to the at least one tracker element in a preoperative scan;
   capturing data indicating the at least one tracker element's position during surgery at an operation site;
   acquiring live images of a surgical site;
   generating a three-dimensional volume model of the patient's region of interest from the at least one at least two-dimensional medical image;
   generating a synthetic cross-sectional image of the volume model in a plane aligned with a plane of a live image; and
   registering and blending the synthetic cross-sectional image and a live image of the live images according to the captured data of the tracker element's position during surgery.

13. The method of claim 12, wherein additively manufacturing at least parts of the patient receiving device (14) comprises additively building a structure (31) comprising an inner shape that is at least partly conformed to the outer contour shape (S) of the patient's body (13) and/or partly deviates from the outer contour shape (S) for bringing the patient's body (13) into a desired position, orientation, and/or shape (D).

\* \* \* \* \*